US010350761B2

(12) United States Patent
Yuki et al.

(10) Patent No.: US 10,350,761 B2
(45) Date of Patent: Jul. 16, 2019

(54) COMMUNICATION DEVICE

(71) Applicant: TOYOTA JIDOSHA KABUSHIKI KAISHA, Toyota-shi (JP)

(72) Inventors: Mina Yuki, Toyota (JP); Shintaro Yoshizawa, Nagoya (JP)

(73) Assignee: TOYOTA JIDOSHA KABUSHIKI KAISHA, Toyota-shi (JP)

(*) Notice: Subject to any disclaimer, the term of this patent is extended or adjusted under 35 U.S.C. 154(b) by 0 days.

(21) Appl. No.: 15/722,204

(22) Filed: Oct. 2, 2017

(65) Prior Publication Data

US 2018/0104822 A1    Apr. 19, 2018

(30) Foreign Application Priority Data

Oct. 13, 2016 (JP) ................................. 2016-202097

(51) Int. Cl.
*B25J 11/00* (2006.01)
*G16H 40/63* (2018.01)
(Continued)

(52) U.S. Cl.
CPC .............. *B25J 11/008* (2013.01); *A63H 3/28* (2013.01); *A63H 11/00* (2013.01); *A63H 13/005* (2013.01);
(Continued)

(58) Field of Classification Search
CPC ........ B25J 11/008; B25J 13/00; B25J 19/023; B25J 9/0003; B25J 9/1697; B25J 5/00;
(Continued)

(56) References Cited

U.S. PATENT DOCUMENTS

2006/0128263 A1* 6/2006 Baird .................. A61B 5/16
446/321
2010/0060713 A1* 3/2010 Snyder .............. G06K 9/00335
348/14.01
(Continued)

FOREIGN PATENT DOCUMENTS

JP      2 331 713 A    6/1999
JP      11-179061 A    7/1999
(Continued)

OTHER PUBLICATIONS

"A cat-shaped communication device 'BN-1'," http://www.bandai.co.jp/catalog/item/4543112005373000.html, Sep. 15, 2016, 1 page.

*Primary Examiner* — Xilin Guo
(74) *Attorney, Agent, or Firm* — Oblon, McClelland, Maier & Neustadt, L.L.P.

(57) ABSTRACT

A communication device includes a display provided in a face portion; an environment information acquisition unit that acquires environment information being information about an environment around the communication device; a gaze motion generation unit that generates a gaze motion of the communication device to be expressed in the face portion, the gaze motion corresponding to the environment information acquired by the environment information acquisition unit; a feeling generation unit that generates, according to a predetermined generation rule, a feeling of the communication device to be expressed in the face portion; and an integration unit that displays on the display an image of an eye expressing the gaze motion generated by the gaze motion generation unit and the feeling generated by the feeling generation unit.

15 Claims, 10 Drawing Sheets

(51) Int. Cl.
  *A63H 11/00* (2006.01)
  *B25J 5/00* (2006.01)
  *B25J 9/00* (2006.01)
  *B25J 9/16* (2006.01)
  *B25J 13/00* (2006.01)
  *B25J 19/02* (2006.01)
  *A63H 3/28* (2006.01)
  *A63H 13/00* (2006.01)

(52) U.S. Cl.
  CPC ............... *B25J 5/00* (2013.01); *B25J 9/0003* (2013.01); *B25J 9/1697* (2013.01); *B25J 11/001* (2013.01); *B25J 13/00* (2013.01); *B25J 19/023* (2013.01); *G16H 40/63* (2018.01); *A63H 2200/00* (2013.01)

(58) Field of Classification Search
  CPC . B25J 11/001; B25J 11/00; B25J 19/02; B25J 9/00; B25J 9/16; A63H 11/00; A63H 3/28; A63H 13/005; A63H 2200/00; G06F 19/3406; G06F 19/00; G06F 3/012; G16H 40/63; G06K 9/00302; G06K 9/00268; G06K 9/00281; G06K 9/00228; G06K 9/00248; G06K 9/00255; G06K 9/00664; G06T 2207/30201; G06T 13/40; G06T 7/20; G06T 7/70; G06N 3/006; H04N 5/23219; H04N 13/383
  See application file for complete search history.

(56) References Cited

U.S. PATENT DOCUMENTS

| | | | |
|---|---|---|---|
| 2015/0018095 A1* | 1/2015 | Segal | A63F 13/30 463/31 |
| 2015/0206465 A1* | 7/2015 | Yoshikawa | G09F 19/08 40/470 |
| 2017/0352351 A1* | 12/2017 | Kimura | A63H 5/00 |

FOREIGN PATENT DOCUMENTS

| | | |
|---|---|---|
| JP | 2006-289507 | 10/2006 |
| JP | 2006-289508 | 10/2006 |
| JP | 2007-69302 A | 3/2007 |
| JP | 2008-018529 | 1/2008 |
| JP | 2013-154458 A | 8/2013 |
| JP | 2016-103277 | 6/2016 |

\* cited by examiner

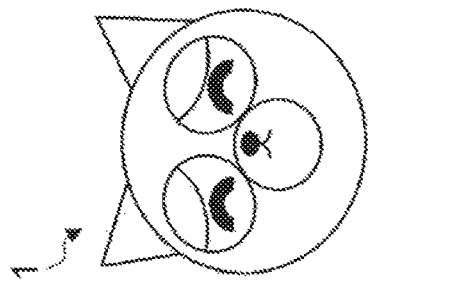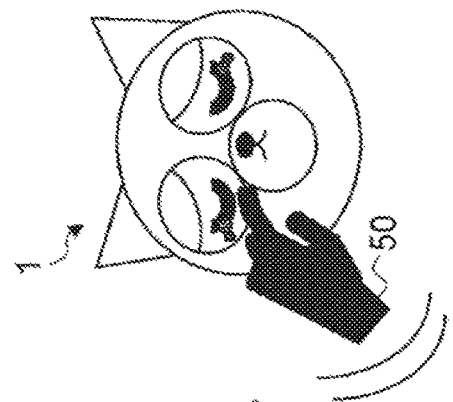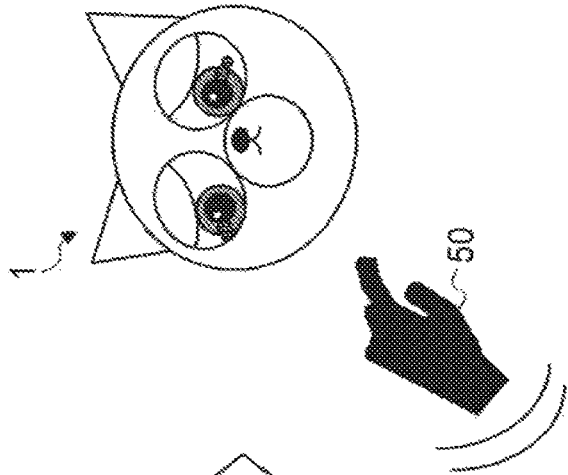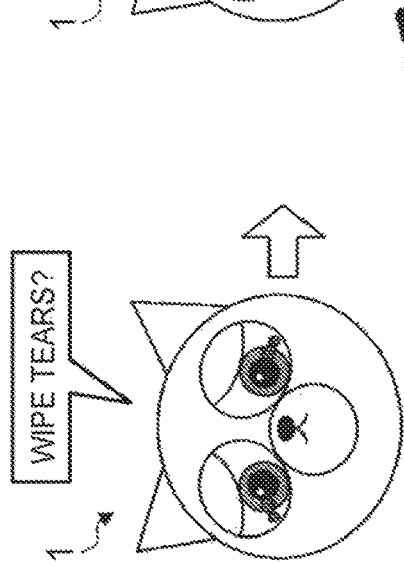

COMMUNICATION DEVICE

INCORPORATION BY REFERENCE

The disclosure of Japanese Patent Application No. 2016-202097 filed on Oct. 13, 2016 including the specification, drawings and abstract is incorporated herein by reference in its entirety.

BACKGROUND

1. Technical Field

The present disclosure relates to a communication device and, in particular, relates to a communication device including a face portion.

2. Description of Related Art

In recent years, communication devices that communicate with users have been developed. In this regard, there has been known a technique that provides a face portion in a communication device and changes display on this face portion.

For example, Japanese Patent Application Publication No. 2016-103277 (JP 2016-103277 A) discloses a robot including a display portion that displays an image of the entire face. Further, Japanese Patent Application Publication No. 2016-289508 (JP 2006-289508 A) discloses a technique that, in a robot including eyelids and eyeballs, expresses a feeling or a line of sight of the robot by changing the opening/closing degree of the eyelids and the inclination degree of the eyelids with respect to the eyeballs.

SUMMARY

Animals including a human being may direct the line of sight to other than a communication partner when, for example, concerned about the state of surrounding environment. Such a gaze motion may also occur while expressing a feeling. Therefore, it is considered that, by integrating expression of such a gaze motion and expression of a feeling, expression of a natural face as an animal made possible. JP 2016-103277 A discloses to express a facial expression, a line of sight, or the like of the robot on the display portion, but it fails to provide a face expression method combining the facial expression and the line of sight. The robot described in JP 2006-289508 A expression a line of sight watching a direction of a sound source by a manner of the eyelids, but, since this robot expresses a feeling by the inclination of the eyelids, it can express only one of the line of sight and the feeling and thus it cannot express the line of sight and the feeling simultaneously.

The present disclosure provides a communication device that enables natural expression of a face.

One aspect of the present disclosure is a communication device including a face portion; a display provided in the face portion; an environment measuring device configured to acquire environment information being information about an environment around the communication device; and a control device, the control device configured to generate a gaze motion of the communication device to be expressed in the face portion, the gaze motion corresponding to the environment information; generate, according to a predetermined generation rule, a feeling of the communication device to be expressed in the face portion; and display on the display an image of an eye expressing the gaze motion and the feeling. In this communication device, an image of an eye expressing the generated gaze motion corresponding to the environment information and the generated feeling is displayed on the display. Therefore, since a facial expression in which a line of sight and a feeling are integrated can be presented, natural expression of a face can be achieved.

In the above-described aspect, the environment measuring device may be configured to acquire, as the environment information, a first direction in which a communication partner is present, and a second direction in which a moving object is present, and the control device may be configured to generate a first gaze motion being a gaze motion to be directed toward the first direction, and a second gaze motion being a gaze motion to be directed toward the second direction; select one of the first gaze motion and she second gaze motion; and display on the display the image of the eye expressing the selected gaze motion and the feeling. According to this configuration, the line of sight watching the moving object present in the surrounding environment can be made as a candidate of a display object. Therefore, it is possible to achieve expression of a face that cares about the state of the surrounding environment.

In the a above-described aspect, in the case where an image of a closed eye is displayed on the display when the environment measuring device acquires the environment information about the moving object, the control device may be configured not to select the second gaze motion and be configured to display on the display the image of the eye expressing the feeling. According to this configuration, in the state where the moving object cannot be visually recognized, the line of sight that is directed toward the direction of the moving object is not displaced. Therefore, it is possible to avoid unnatural display.

In the above-described aspect, the environment measuring device may be configured to acquire, as the environment information, a first direction in which a communication partner is present, and a third direction being a direction of a sound generated in the environment around the communication device, and the control device may be configured to generate a first gaze motion being a gaze motion to be directed toward the first direction, and a third gaze motion being a gaze motion to be directed toward the third direction; select one of the first gaze motion and the third gaze motion; and display on the display the image of the eye expressing the selected gaze motion and the feeling. According to this configuration, the line of sight that is directed toward the third direction can be made as a candidate of a display object. Therefore, it is possible to achieve expression of a face that cares about the state of the surrounding environment.

In the above-described aspect, the control device may be configured to select the first gaze motion when a feeling being an expression object corresponds to a predetermined feeling. According to this configuration, it can be avoided that a line of sight directed to other than the communication partner is expressed in feeling expression in which such a line of sight is unnatural. Therefore, it is possible so present natural facial expression.

In the above-described aspect, the control device may be configured to determine a dialogue consent wish a communication partner; and generate a gaze motion corresponding to the determined dialogue content. According to this configuration, it is possible to display the line of sight corresponding to the dialogue content along with the feeling. Therefore, expression of the feeling can be assisted by the line of sight corresponding to the dialogue content, so that feeling expression can be made rich.

In the above-described aspect, a display screen of the display may have a size and a shape corresponding to those of the eye that is expressed in the face portion. According to this configuration, any of portions, other than the eye, of the face of the communication device does not need to be formed by the display. Therefore, for example, the portions of the face, other than the eye, can be formed by more realistic member. Consequently, it is possible to improve the degree of design freedom of portions, other than the eye, of the face.

According to the present disclosure, it is possible to provide a communication device that enables natural expression of a face.

BRIEF DESCRIPTION OF THE DRAWINGS

Features, advantages, and technical and industrial significance of exemplary embodiments will be described below with reference to the accompanying drawings, in which like numerals denote like elements, and wherein:

FIGS. 10A to 10D are exemplary diagrams showing an example of use of the communication device including touch with a communication partner;

DETAILED DESCRIPTION OF EMBODIMENTS

Figure 1:
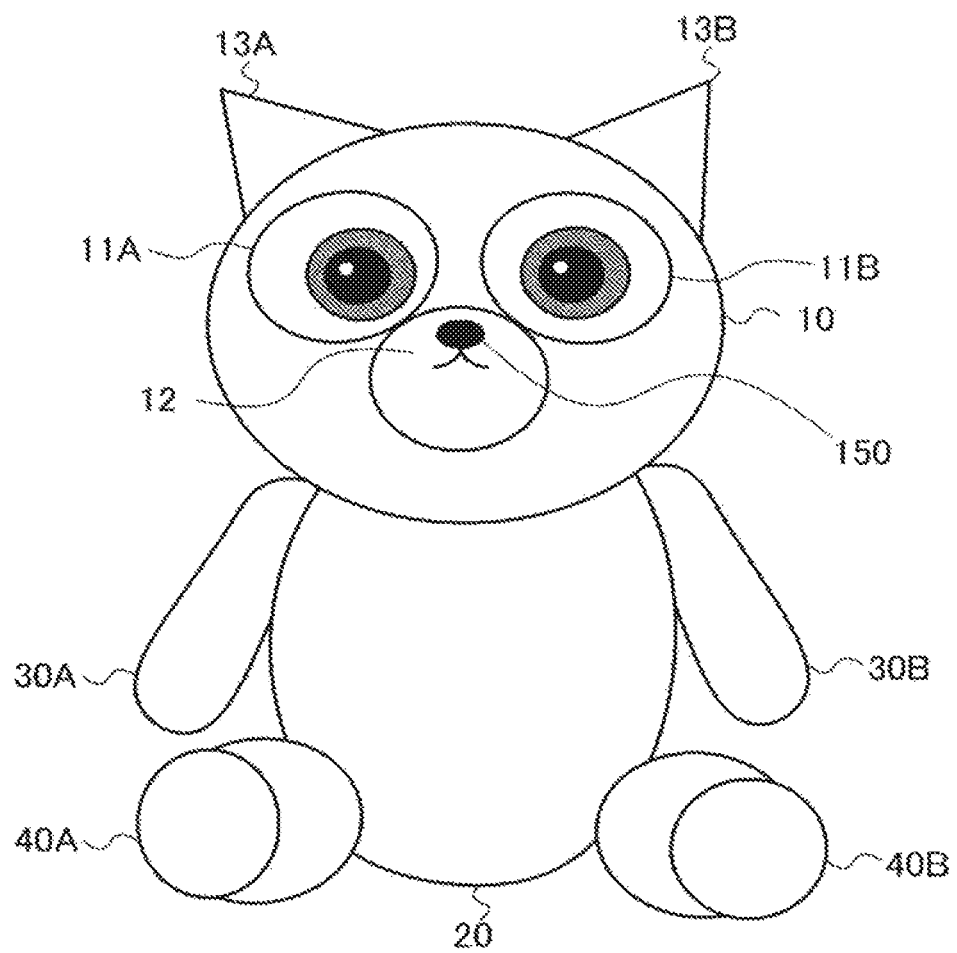
FIG. 1 is a front view of a communication device according to an embodiment.

Hereinbelow, an embodiment of the present disclosure will be described with reference to the drawings. FIG. 1 is a front view of a communication device 1 according to the embodiment. As shown in FIG. 1, the communication device 1 according to this embodiment is a device having an external appearance resembling an animal and includes a face portion 10, a trunk portion 20, arm portions 30A and 30B, and leg portions 40A and 40B.

As shown in FIG. 1, the face portion 10 includes displays 11A and 11B as eye portions, a nose portion 12, ear portions 13A and 13B, and so on. The display 11A forms a right eye of a face of the communication device 1. A display screen (display panel) of the display 11A has a size and a shape corresponding to those of a right eye that is expressed in the face portion 10. Likewise, the display 11B forms a left eye of the face of the communication device 1. A display screen (display panel) of the display 11B has a size and a shape corresponding to those of a left eye that is expressed in the face portion 10. That is, in the communication device 1, the face portion 10 is not entirely formed by a display, but only the portions corresponding to the eyes in the face portion 10 are formed by the displays 11A and 11B. In the communication device 1, the portion, other than the eyes, of the face portion 10 are formed by members, other than a display, resembling the components of the face. In this way, in this embodiment, any of the portions, other than the eyes, of the face of the communication device 1 is not formed by a display. Therefore, the portions of the face, other than the eyes, can be formed by more realistic members. Further, when the face portion 10 is entirely formed by a display, it is difficult to provide various sensors such as a later-described camera 150 in the face portion 10, but, in this embodiment, since the range formed by the displays is limited, it is possible to improve the degree of design freedom.

Hereinbelow, when referring to the display 11A and the display 11B without particularly distinguishing between them, the displays 11A and 11B will be referred to simply as the display 11. The display panel of the display 11 is, for example, a liquid crystal panel, but is not limited thereto, and a display having another configuration may alternatively be used.

Figure 2:
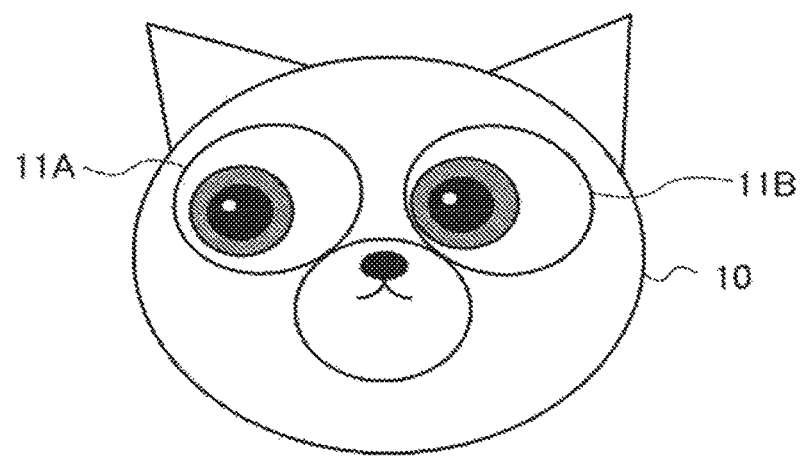
FIG. 2 is a diagram showing an example in which an image expressing a line of sight watching right is displayed in the communication device according to the embodiment.

The displays 11A and 11B respectively display images of the eyes. Therefore, the line of sight of the communication device 1 can be expressed by display on the display 11 as shown in FIG. 2. FIG. 2 shows an example in which an image expressing a line of sight watching right is displayed. Note that an image of an eye may include not only an image of an eyeball, but also an image of a component relating to the eye, such as an eyelid, an eyebrow, or a tear.

In this embodiment, in order to resemble a nose of the animal, the nose portion 12 protrudes forward in the face portion 10. At a protruding end of the nose portion 12, the camera 150 that functions as a later-described environment measuring device 15 is provided. In this embodiment, since the camera 150 is provided at the protruding position of the face portion 10, it is possible to look around the communication device 1 from the camera 150. Therefore, the camera 150 can well capture an image of an environment around the communication device 1.

The ear portions 13A and 13B are each provided with a microphone (not shown) that functions as the later-described environment measuring device 15. By these microphones, the sound of an environment around the communication device 1 is measured. The microphone may be provided in only one of the ear portions 13A and 13B, or may be provided at a portion other than the ear portions 13A and 13B in the face portion 10, or may be provided at a portion other than the face portion 10 in the communication device 1.

Figure 3:
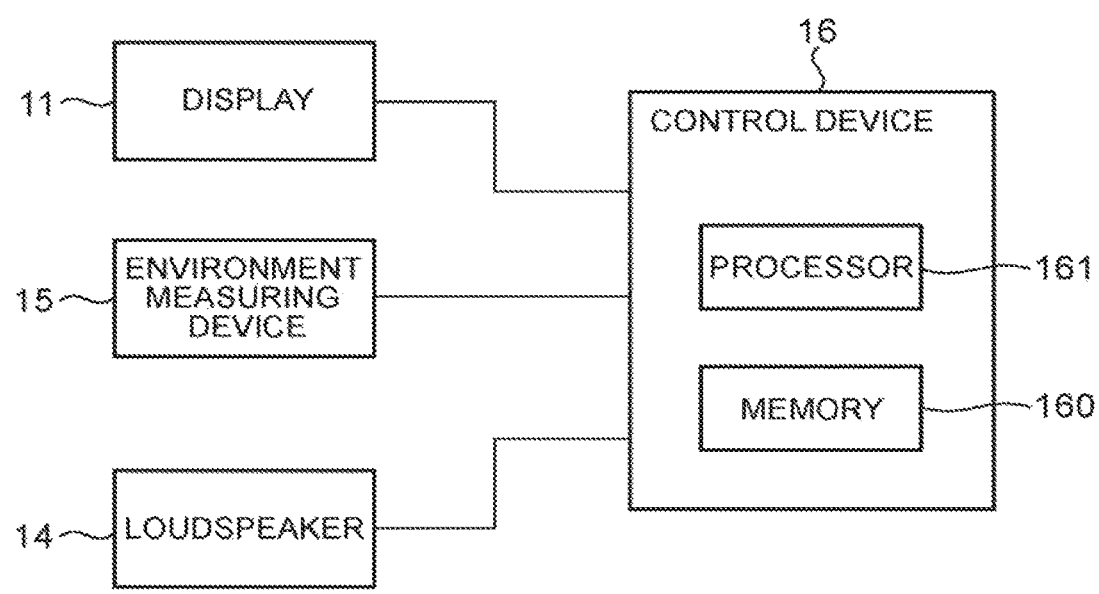
FIG. 3 is a block diagram showing one example of a hardware configuration of the communication device according to the embodiment.

Next, the hardware configuration of the communication device 1 will be described. FIG. 3 is a block diagram showing one example of a hardware configuration of the communication device 1. As shown in FIG. 3, the communication device 1 includes the display 11, a loudspeaker 14, the environment measuring device 15, and a control device 16.

The display 11 displays an image of the eyes according to control of the control device 16. The loudspeaker 14 outputs a voice or the like according to control of the control device 16. Consequently, the communication device 1 can talk to a communication partner.

The environment measuring device 15 is a device that measures a surrounding environment in order to acquire information about an environment around the communication device 1. Specifically, the environment measuring device 15 includes the camera 150 and the microphones. The environment measuring device 15 outputs measured data to the control device 16. Therefore, the environment measuring device 15, for example, captures an image of a surrounding environment including a communication partner. Further, the environment measuring device 15, for example, detects a voice uttered by a communication partner, a sound in a surrounding environment, or the like. The environment measuring device 15 is satisfactory as long as it is a device that can measure a surrounding environment, and thus is not limited to the camera 150 and the microphones. For example, the environment measuring device 15 may be a distance sensor, such as a laser range finder, that measures the distance to an object.

The control device 16 includes a memory 160 and a processor 161. For example, the memory 160 is formed by a combination of a volatile memory and a nonvolatile memory. The memory 160 is used for storing software (computer program) to be executed by the processor 162, and so on.

This program can be stored in any of non-transitory computer-readable media of various types and supplied to a computer. The non-transitory computer-readable media include various types of tangible storage media. Examples of the non-transitory computer-readable media include magnetic recording medium (e.g. flexible disk, magnetic tape, hard disk drive), magneto-optical recording medium (e.g. magneto-optical disk), compact disc-read only memory (CD-ROM) CD-R, CD-R/W, and semiconductor memory (e.g. mask ROM, programmable ROM (PROM), erasable PROM (EPROM), flash ROM, random-access memory (RAM)). Alternatively, the program may be supplied to a computer by any of transitory computer-readable media of various types. Examples of the transitory computer-readable media include electrical signal, optical signal, and electromagnetic wave. The transitory computer-readable medium can supply the program to the computer via a wired communication path such as an electric wire or an optical fiber, or a wireless communication path.

Figure 4:
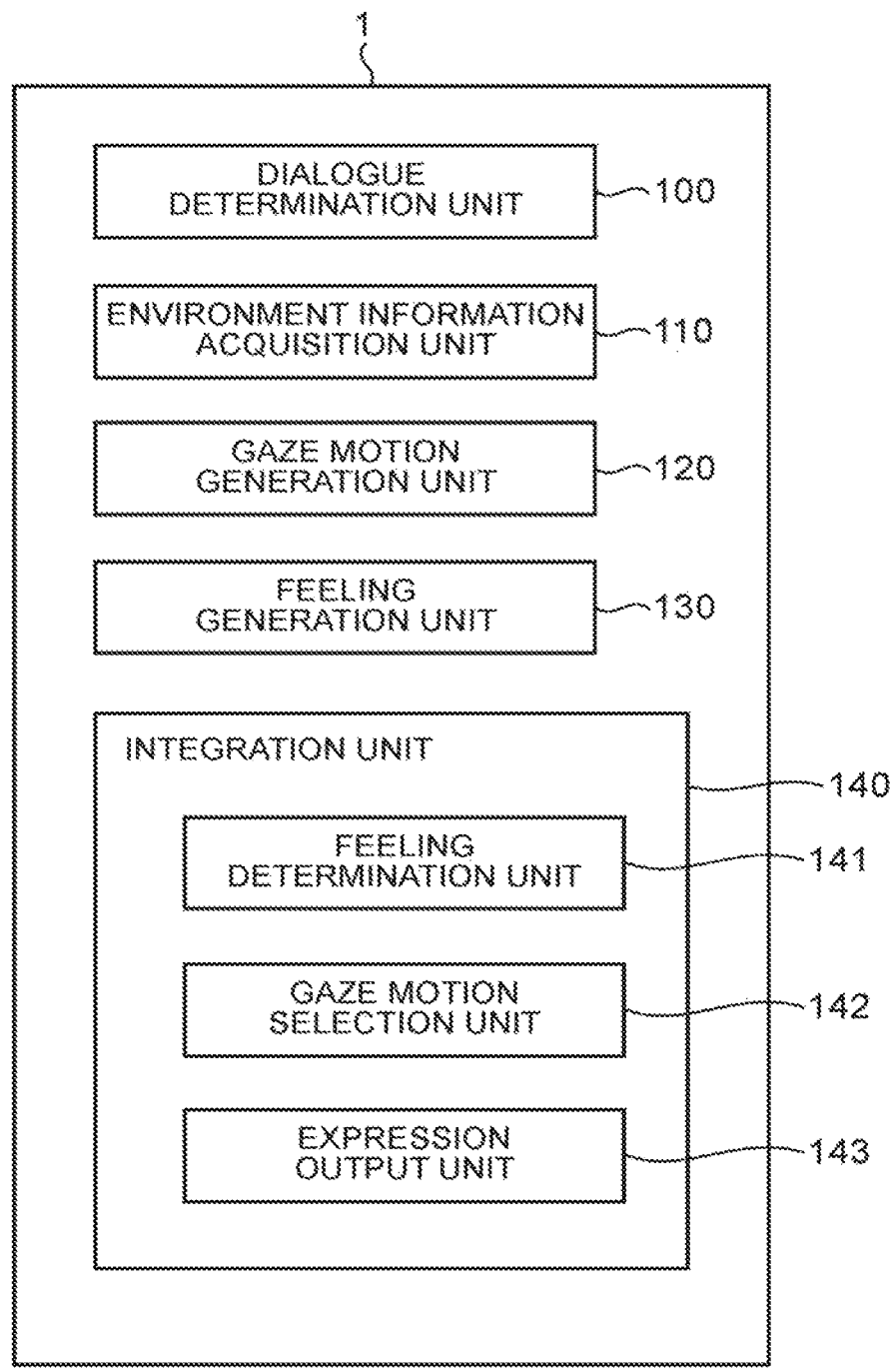
FIG. 4 is a block diagram showing one example of a software configuration of the communication device according to the embodiment.

The processor 161 reads the software (computer program) from she memory 160 and executes it, thereby performing processing of later-described units shown in FIG. 4. In this way, the control device 16 functions as a computer. The processor 161 may be, for example, a microprocessor, a MPU (micro processing unit), or a CPU (central processing unit). The processor 161 may include a plurality of processors.

Next, the configuration of the communication device 1 created by execution of the software by the processor 161 will be described. FIG. 4 is a block diagram showing one example of a software configuration of the communication device 1. As shown in FIG. 4, the communication device 1 includes a dialogue determination unit 100, an environment information acquisition unit 110, a gaze motion generation unit 120, a feeling generation unit 130, and an integration unit 140. The dialogue determination unit 100 may be called a dialogue determination means, the environment information acquisition unit 110 may be called an environment information acquisition means, the gaze motion generation unit 120 may be called a gaze motion generation means, the feeling generation unit 130 may be called a feeling generation means, and the integration unit 140 may be called a display control means.

The dialogue determination unit 100 determines whether or not the communication device 1 is in dialogue with a communication partner. For example, when the volume of a voice of a partner detected by the microphones has exceeded a predetermined threshold value, the dialogue determination unit 100 determines that the communication device 1 is in dialogue with a communication partner. The dialogue determination unit 100 may also determine a dialogue content with the communication partner. The dialogue content is determined, for example, from an analysis result of a voice detected by the microphones or from a voice content uttered by the communication device 1 to the communication partner.

The environment information acquisition unit 110 acquires environment information being information about an environment around the communication device 1. Specifically, the environment information acquisition unit 110 acquires environment information by analyzing data obtained from the environment measuring device 15. For example, the environment information acquisition unit 110 acquires, as environment information, information about a direction (first direction) in which the communication partner is present, information about a presence direction (second direction) of a moving object present in an environment around the communication device 1, and so on. More specifically, for example, the environment information acquisition unit 110 acquires, as environment information, a position of the communication partner, a position of the object, the presence/absence of movement of them, and so on. For example, the environment information acquisition unit 110 recognizes a position of a face of the communication partner form a captured image of the camera 150 by image processing using feature points of a face of a person, thereby detecting a position of the communication partner or its movement. For example, when, after recognizing the communication partner, a moving object other than the communication partner has entered in an image capture range of the camera 150, the environment information acquisition unit 110 recognizes this moving object as an object other than the communication partner, thereby detecting a position of this object or its movement.

Further, the environment information acquisition unit 110 acquires, as environment information, sound information generated in an environment around the communication device 1. For example, the environment information acquisition unit 110 analyzes a sound detected by the microphones and acquires, as environment information, a generation direction (third direction) of a sound generated in an environment around the communication device 1. The environment information acquisition unit 110 may acquire, as environment information, a generation direction of a sound exceeding a predetermined level.

An arbitrary technique can be used for acquiring environment information. For example, information about a communication partner and an object may be acquired by making a comparison between an image of an environment around the communication device 1 captured in advance and an image captured at the time of acquiring environment information.

The gaze motion generation unit 120 generates a gaze motion (more specifically, a parameter indicative of a gaze motion) of the communication device 1 that is expressed in the face portion 10. In this event, the gaze motion generation unit 120 generates a gaze motion corresponding to the environment information acquired by the environment information acquisition unit 110. For example, the gaze motion generation unit 120 generates a gaze motion (first gaze motion) to watch the communication partner, a gaze motion (second gaze motion) to watch the direction in which the moving object is present, a gaze motion (third gaze motion) to watch the direction in which the sound is generated, and so on. When the communication partner is not found, the gaze motion generation unit 120 may generate a gaze motion to search for the communication partner. The gaze motion to watch the communication partner is, in other words, a gaze motion to watch the direction in which the communication partner is present, and specifically, is, for example, a gaze motion to watch the direction in which the face of the communication partner is present. The gaze motion generation unit 120 outputs the generated gaze motions to the integration unit 140. The gaze motions generated by the gaze motion generation unit 120 are gaze motion candidates to be displayed on the display 11, and whether or not the gaze motions generated by the gaze motion generation unit 120 are displayed on the display 11 is determined by the later-described integration unit 140. In this way, since the gaze motions corresponding to the environment information are generated, it is possible to express that the communication device 1 visually recognizes the communication partner and recognizes the surrounding environment. Therefore, it is possible to realize rich expression of the face portion 10 and thus to make the user feel an attachment and affinity to the communication device 1.

The feeling generation unit 130 generates, according to a predetermined generation rule, a feeling (more specifically, a parameter indicative of a feeling) of the communication device 1 that is expressed in the face portion 10. Since the feeling is generated by the feeling generation unit 130 and expressed by the later-described integration unit 140, it is possible to transmit a mood, a state, or the like of the communication device 1 to the communication partner. Therefore, it is possible to assist the communication to go smoothly. It is also possible to suppress that the user gets tired of the communication device 1. The following can be given as generation rules by way of example only and are not to be taken by way of limitation.

First, there is given a generation rule that estimates a feeling of a communication partner from a face of the communication partner acquired from a captured image of the camera 150 and generates as a feeling of the communication device 1 a feeling that sympathizes with the feeling of the communication partner. That is, in this case, the feeling generation unit 130 generates a feeling corresponding to the face of the communication partner. This makes it possible to display a feeling corresponding to a feeling of the communication partner. Therefore, it is possible to realize natural communication with the communication partner. Estimation of a feeling can be performed, for example, by pattern matching between predetermined face images and a captured image of the camera 150.

Second, there is given a generation rule that estimates a feeling of a communication partner from a dialogue content determined by the dialogue determination unit 100 and generates as a feeling of the communication device 1 a feeling that sympathizes with the feeling of the communication partner. That is, in this case, the feeling generation unit 130 generates a feeling corresponding to a dialogue content determined by the dialogue determination unit 100. This makes it possible to display a feeling corresponding to the dialogue content. Therefore, it is possible to realize natural communication with the communication partner. Estimation of a feeling can be performed, for example, by pattern matching between predetermined conversation contents and a dialogue content determined by the dialogue determination unit 100.

Third, there is given a generation rule that generates a spontaneous feeling from an internal state of the communication device 1. That is, in this case, the feeling generation unit 130 generates a feeling corresponding to the internal state. This makes it possible to display a spontaneous feeling. The internal state is, for example, the decreasing degree of the remaining capacity of a battery that supplies electric power to the communication device 1, or the continuous use time of the communication device 1. For example, the feeling generation unit 130 may generate a feeling such as fatigue according to the internal state.

Fourth, there is given a generation rule that generates a feeling of the communication device 1 based on an action (e.g. behavior, hand gesture) of a communication partner acquired from a captured image of the camera 150. According to this generation rule, for example, a feeling is generated that is correlated with a predetermined action in advance. That is, in this case, the feeling generation unit 130 generates a feeling corresponding to an action of the communication partner. This makes it possible to display a feeling responding to an action of the communication partner.

The feeling generation unit 130 may generate a plurality of feelings simultaneously based on these generation rules. The feeling generation unit 130 outputs the generated feelings to the integration unit 140.

Figure 5:
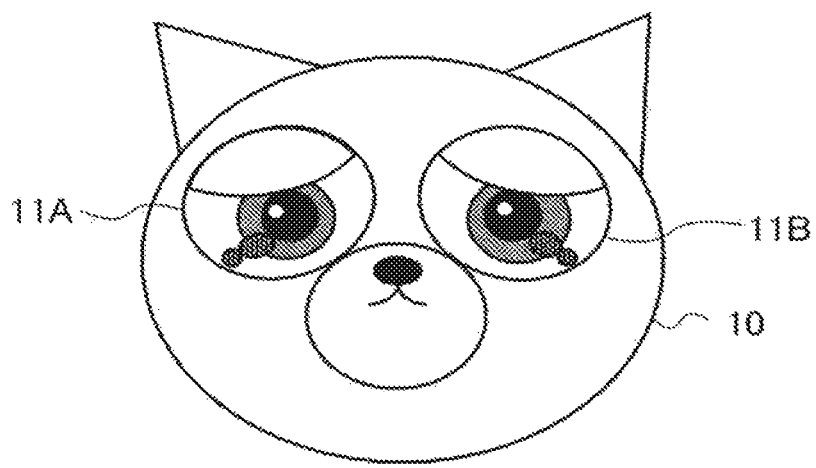
FIG. 5 is a diagram showing a display example when expressing a negative feeling in a face expression.
Figure 6:
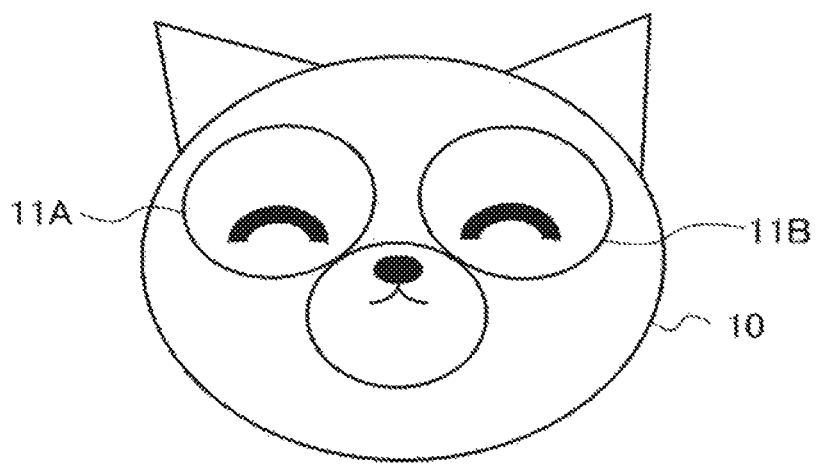
FIG. 6 is a diagram showing a display example when expressing a positive feeling in the face portion.

As a simple configuration, the feeling generation unit 130 generates, for example, one or both of positive and negative two feelings, but the kinds of feelings are not limited thereto. By increasing the kinds of feelings that can be generated by the feeling generation unit 130, it is possible to realize richer feeling expression in the communication device 1. In this embodiment, when expressing a negative feeling in the face portion 10, an image of weeping eyes is displayed on the display 11 as shown in FIG. 5. In this embodiment, when expressing a positive feeling in the face portion 10, an image showing a smiling state with closed eyes is displayed on the display 11 as shown in FIG. 6.

The integration unit 140 performs control to display on the display 11 an image of the eyes expressing the gaze motion generated by the gaze motion generation unit 120 and the feeling generated by the feeling generation unit 130. However, when an image of the eyes expressing the feeling being the expression object is an image of closed eyes, the integration unit 140 does not use as a display object the gaze motion generated by the gaze motion generation unit 120 and uses only the feeling as a display object. Hereinbelow, the specific configuration of the integration unit 140 will be described. As shown in FIG. 4, the integration unit 140 includes a feeling determination unit 141, a gaze motion selection unit 142, and an expression output unit 143.

When there are a plurality of feelings generated by the feeling generation unit 130, the feeling determination unit 141 determines one from these feelings. The feeling determination unit 141 may determine one of the feelings by an arbitrary method. For example, the feeling determination unit 141 may select one of the feelings, generated by the feeling generation unit 130, according to a predetermined selection rule. Alternatively, the feeling determination unit 141 may apply a weight to the feeling per generation rule and determine one feeling by integrating the plurality of feelings. Weighting values and selection rules may be designated by a user such as a medical worker or a caregiver.

The gaze motion selection unit 142 selects one from the gaze motions generated by the gaze motion generation unit 120. For example, when the gaze motion to watch the communication partner and the gaze motion corresponding to the surrounding environment are generated by the gaze motion generation unit 120, the gaze motion selection unit 142 selects which of the gaze motions should be an expression object. The gaze motion selection unit 142 may make the selection by an arbitrary method. For example, the gaze motion selection unit 142 may make the selection according to the feeling determined by the feeling determination unit 141, or may make the selection according to the environment information acquired by the environment information acquisition unit 110, or may make the selection based on another factor. To give a more specific example, the gaze motion selection unit 142 may select the gaze motion according to whether or not the feeling determined by the feeling determination unit 141 corresponds to a predetermined feeling. For example, when a feeling of the communication device 1 is anger, it is supposed that the communication device 1 is not conscious of an ambient sound or a moving object. By selecting a gaze motion based on a feeling, it is possible to realize such nature of an animal. The gaze motion selection unit 142 may select the gaze motion to watch the sound source direction when the volume of the sound acquired by the environment information acquisition unit 110 is equal to or more than a predetermined level, and may select the gaze motion to watch the communication partner when it is less than the predetermined level. The gaze motion selection unit 142 may select the gaze motion to watch the presence direction of the moving object or the sound source when the dialogue duration period with the communication partner is less than one week, and may select the gaze motion to watch the communication partner when it is one week or more. The reason for performing such control according to the dialogue duration period is that when closeness to the communication partner is low (i.e. when the dialogue duration period is short), it is supposed that the degree of concentration to communication is low.

The gaze motion selection unit 142 may determine whether or not it is unnatural to move the line of sight while expressing the feeling determined by the feeling determination unit 141. Herein, an example of being unnatural will be described. For example, when a feeling that is expressed by the communication device 1 is a particular feeling such as anger or surprise, it is unnatural to express a gaze motion responding to movement of an object or a sound in a surrounding environment. In such a case, it is natural not to move the line of sight watching the communication partner. In order to realize this control, the gaze motion selection unit 142 determines it to be unnatural, for example, when the feeling being an expression object, i.e. the feeling determined by the feeling determination unit 141, corresponds to a predetermined feeling. In this event, the gaze motion to watch the communication partner is selected by the gaze motion selection unit 142. Whether or not it is unnatural may be defined in advance for each of feelings that can be expression objects, and the gaze motion selection unit 142 may make a determination by referring to this definition information.

The following case also corresponds to an example of being unnatural. In the case where an image of closed eyes, as shown in FIG. 6, is displayed on the display 11 when the environment information acquisition unit 110 acquires environment information about a moving object, the gaze motion to watch the presence direction of the moving object is unnatural. This is because it is unnatural to visually recognize the moving object in the state where the eyes are closed. Therefore, in this case, the gaze motion selection unit 142 does not select the gaze motion to watch the direction in which the moving object is present. Accordingly, the later-described expression output unit 143 does not select the gaze motion to watch the direction in which the moving object is present, and displays, on the display 11, an image of the eyes expressing the feeling generated by the feeling generation unit 130. That is, in this case, the expression output unit 143 displays the feeling along with the gaze motion such as the gaze motion to watch the communication partner, not the gaze motion to watch the direction in which the moving object is present, or displays the feeling expressed by an image of closed eyes. By performing such control, it is possible to prevent display of the line of sight that is directed toward the direction of the moving object in the state where the moving object cannot be visually recognized. Therefore, it is possible to avoid unnatural display.

In this way, since unnatural expression is prevented, it is possible to suppress giving a sense of incongruity to the communication partner, so that the user tends to feel an attachment and affinity to the communication device 1.

The expression output unit 143 performs output control to display on the display 11 an image of the eyes expressing the gaze motion selected by the gaze motion selection unit 142 and the feeling determined by the feeling determination unit 141. As one example, the expression output unit 142 performs output control as follows. In an example given below, it is assumed that image data corresponding to combination of gaze motions and feelings are stored in the memory 160 in advance. The expression output unit 142 reads from the memory 160 image data corresponding to commands of the gaze motion selection unit 142 and the feeling determination unit 141 and outputs the image data to the display 11.

Figure 7:
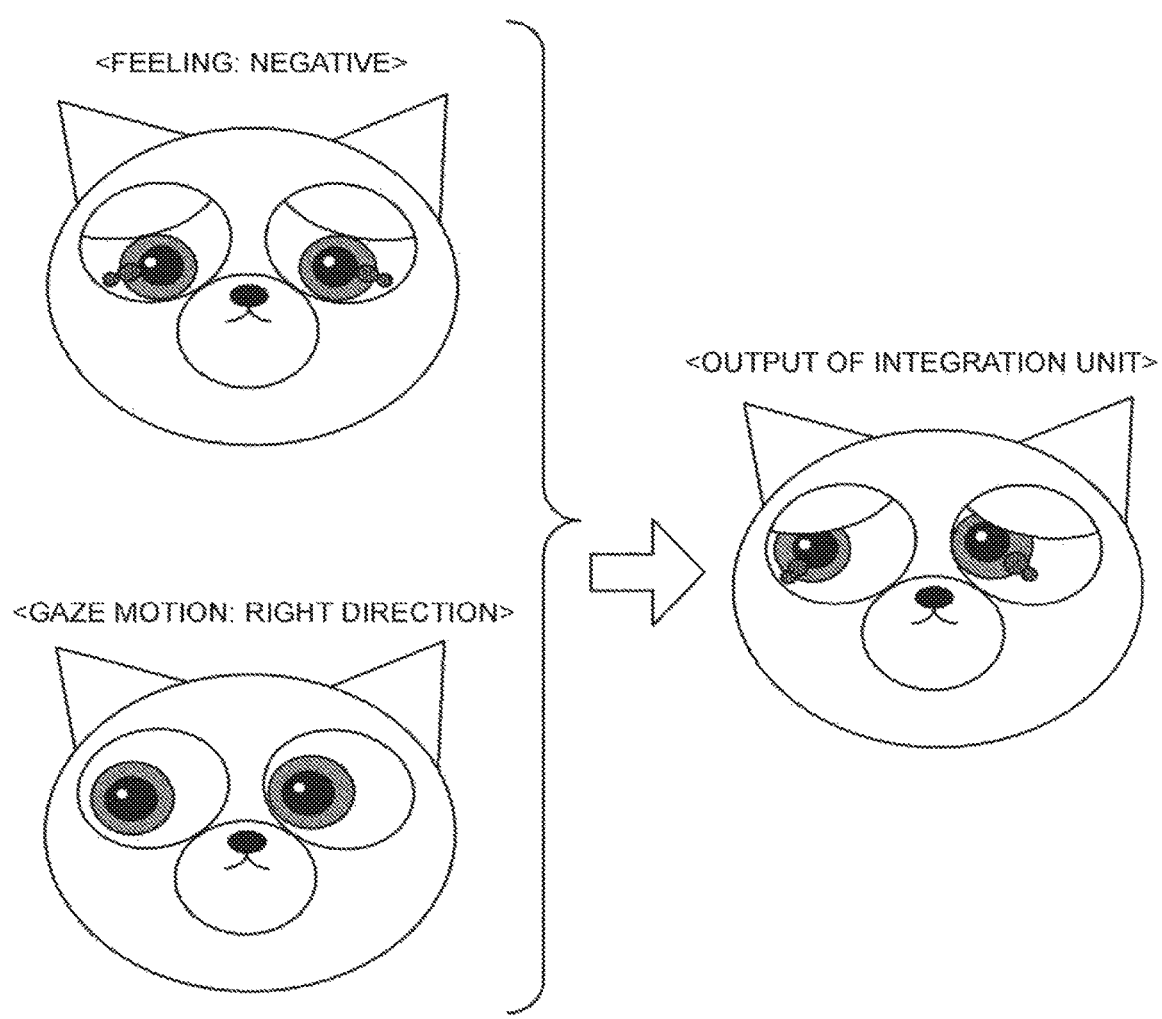
FIG. 7 is an schematic diagram showing one example of integration of a feeling and a line of sight by an integration unit.

FIG. 7 is an exemplary diagram showing one example of the integration of a feeling and a line of sight by the integration unit 140. FIG. 7 shows an example when "negative" is determined as a feeling being an expression object by the feeling determination unit 141, and a gaze motion to watch the right direction is selected as a gaze motion being an expression object by the gaze motion selection unit 142. In this case, the integration unit 140 displays on the display 11 an image of weeping eyes directed toward the right direction.

Figure 8:
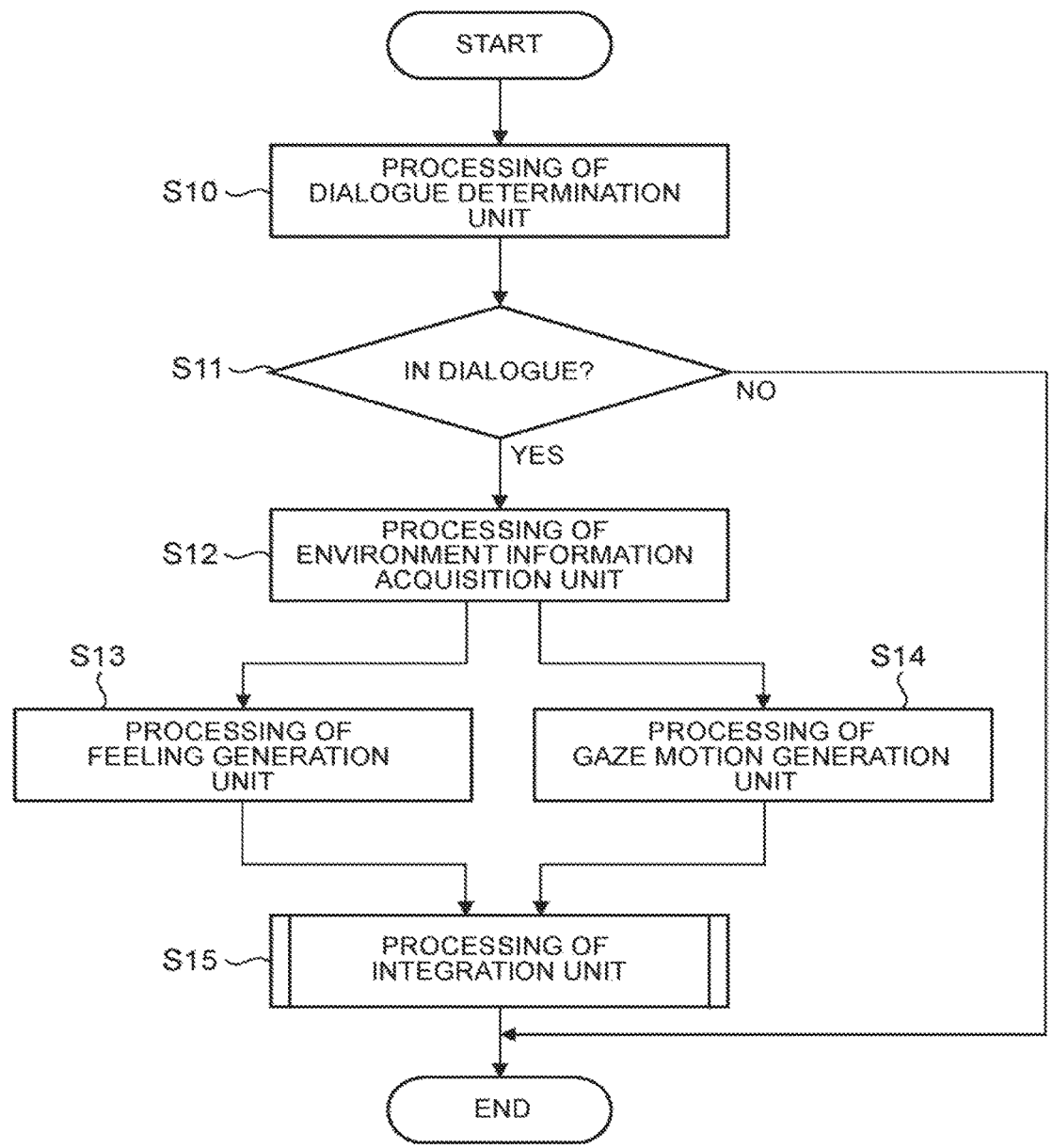
FIG. 8 is a flowchart showing the flow of processing of the communication device according to the embodiment.

Next, the flow of processing in the communication device 1 will be described. FIG. 8 is a flowchart showing the flow of processing of the communication device 1. The communication device 1 repeats the flow shown in FIG. 8. Consequently, for example, it is possible to change from a state where an image of weeping eyes with a line of sight watching a communication partner is displayed, to a state where am image of weeping eyes with a line of sight directed to other than the communication partner is displayed.

Hereinbelow, the flow of processing will be described with reference to the flowchart shown in FIG. 8. First, determination processing by the dialogue determination unit 100 is performed (S10) to determine whether or not the communication device 1 is in dialogue with a communication partner (S11). When not in dialogue (Not at S11), the processing for outputting a facial expression is ended. Accordingly, since display control when not in dialogue can be omitted, it is possible to suppress the consumption of electric power of the battery. When in dialogue (Yes at S11), processing by the environment information acquisition unit 110 is performed (S12). Subsequently, processing by the feeling generation unit 130 (S13) and processing by the gaze motion generation unit 120 (S14) are performed. The processing by the feeling generation unit 130 (S13) and the processing by the gaze motion generation unit 120 (S14) may be performed in parallel, or either one of them may be performed before the other processing. Finally, processing by the integration unit 140 is performed (S15).

Figure 9:
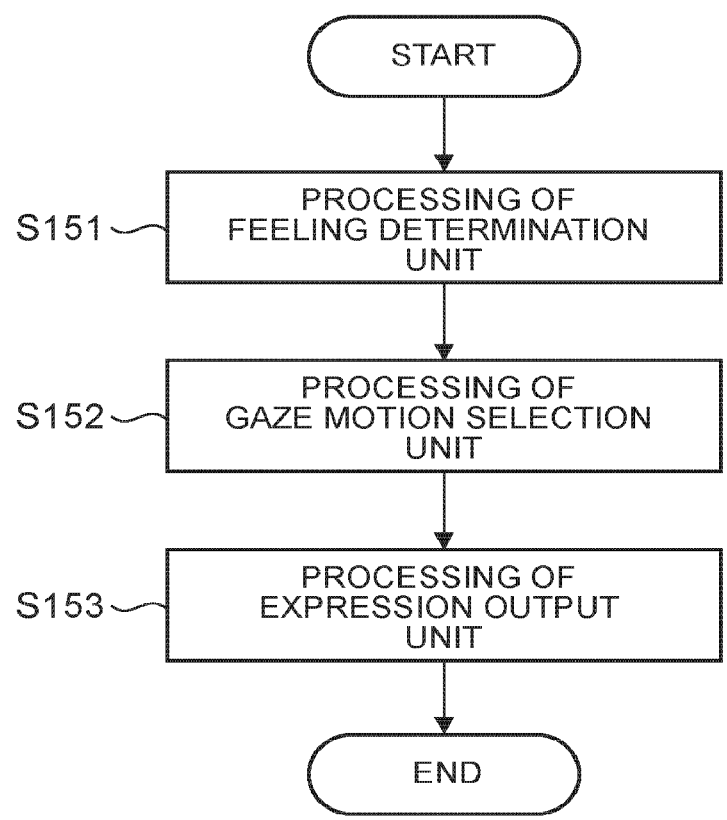
FIG. 9 is a flowchart showing the flow of processing by the integration unit.

FIG. 9 is a flowchart showing the flow of processing by the integration unit 140. Hereinbelow, the flow of processing by the integration unit 140 will be described with reference to FIG. 9. First, processing by the feeling determination unit 141 is performed (S151). Then, processing by the gaze motion selection unit 142 is performed (S152). The processing by the feeling determination unit 141 (S151) and the processing by the gaze motion selection unit 142 (S152) may be performed in parallel, or the processing by the gaze motion selection unit 142 (S152) may be performed before the processing by the feeling determination unit 141 (S151). Thereafter, processing by the expression output unit 143 is performed (S153).

The flow of processing of the communication device 1 has been described above. In the communication device 1, an image of eyes expressing a line of sight corresponding to environment information generated by the gaze motion generation unit 120 and a feeling generated by the feeling generation unit 130 is displayed on the display 11. Therefore, since a facial expression in which the line of sight and the feeling are integrated can be presented, natural expression of a face can be achieved. The gaze motion generation unit 120 generates gaze motions to watch the presence directions of a moving object and a sound source that are present in a surrounding environment. Therefore, it is possible to achieve expression of a face that cares about the state of the surrounding environment. That is, it is possible to express that the communication device 1 recognizes the surrounding environment. Further, in the communication device 1, a line of sight watching a communication partner is selected when a feeling being an expression object is a predetermined feeling. Therefore, it can be avoided that the line of sight is directed to other than the communication partner in feeling expression in which it is unnatural to direct the line of sight in other than the communication partner. Consequently, it is possible in present more natural facial expression.

The communication device 1 may be used for dialogue with a communication partner, and further, may be used including touch with the communication partner. By including touch, deeper communication can be realized. When the communication device 1 resembles an animal, the effect of animal therapy is also expected by including touch.

Figure 11:
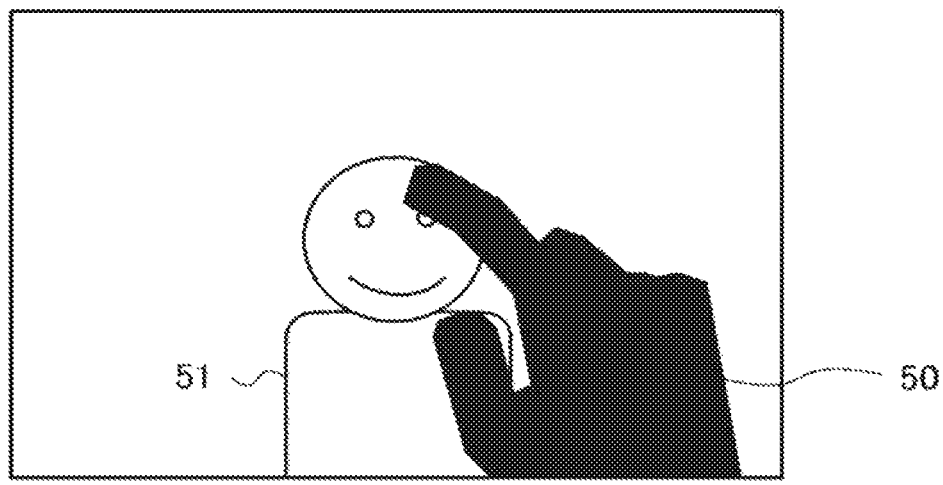
FIG. 11 is a diagram showing one example of a captured image by a camera.

FIG. 10A to 10D are exemplary diagrams showing an example of use of the communication device 1 including touch with a communication partner. In the use example shown in FIGS. 10A to 10D, first, the communication device 1 displaying weeping eyes outputs in voice "Wipe tears?" in order to prompt touch (see FIG. 10A). What a communication partner responding to this holds out a hand 50, the communication device 1 displays weeping eyes while watching a direction of the hand 50 being a moving object (see FIG. 10B). As shown in FIG. 11, when the hand 50 is held out, the camera 150 captures, for example, an image of a communication partner 51 and the hand 50 of the communication partner 51. Therefore, environment information such as a position of the hand 50 is acquired. Subsequently, when the ratio of a region occupied by the hand 50 in an captured image by the camera 150 becomes equal to or more than a predetermined value (e.g., half), the communication device 1 recognizes that the hand 50 is present at close range, and switches to a display of closed eyes (see FIG. 10C). Then, when the hand 50 is moved away, the communication device 1 switches to a display of another feeling (see FIG. 10D). In this embodiment, the change of the line of sight from FIG. 10A to FIG. 10B occurs by transition of gaze motions selected by the gaze motion selection unit 142, while the switching of the display from FIG. 10B to FIG. 10D occurs by transition of feelings determined by the feeling determination unit 141. In the example shown in FIGS. 10A to 10D, by requesting the communications partner to "Wipe tears?", touch is positively prompted. Therefore, touch between the communication device 1 and the communication partner occurs, so that it is possible to facilitate the therapy effect. Further, in this event, since the communication device 1 recognizes the hand of the communication partner and directs the line of sight toward the direction of the hand, it is possible to transmit that the communication device 1 accurately recognizes the approach from the communication partner. Consequently, it is possible to give the communication partner an impression of communicating with a real animal.

Figure 12:
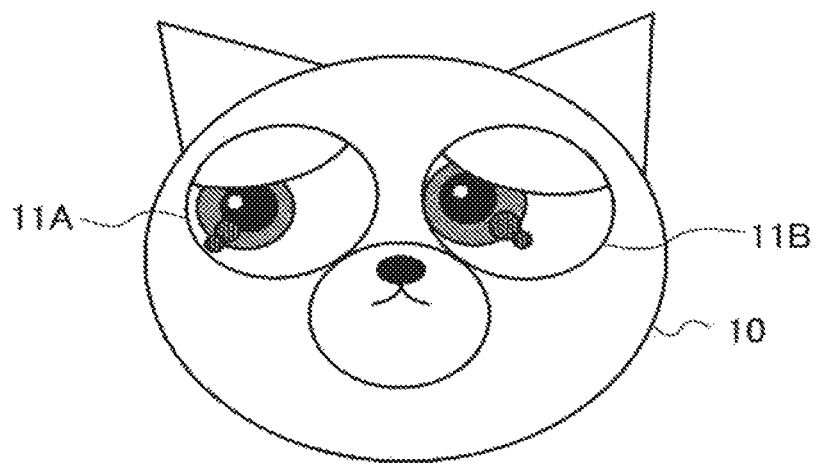
FIG. 12 is a diagram showing a display example when expressing a state of weeping without looking into the eyes of a communication partner.
Figure 13:
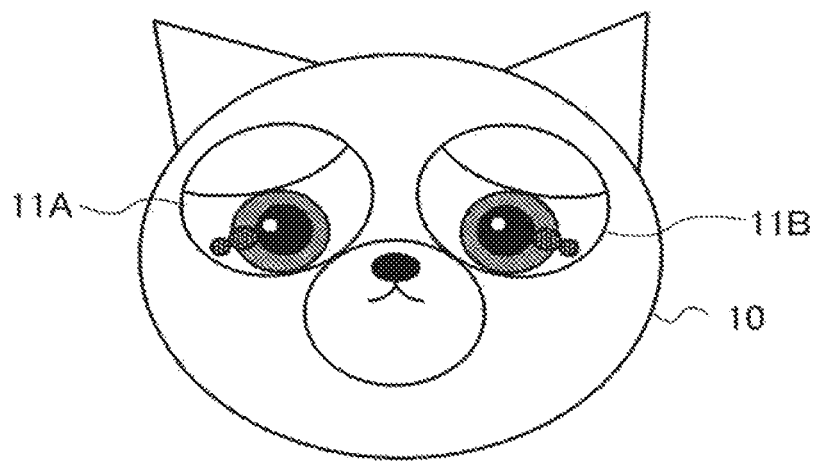
FIG. 13 is a diagram showing a display example when expressing a state of weeping without looking into the eyes of a communication partner.
Figure 14:
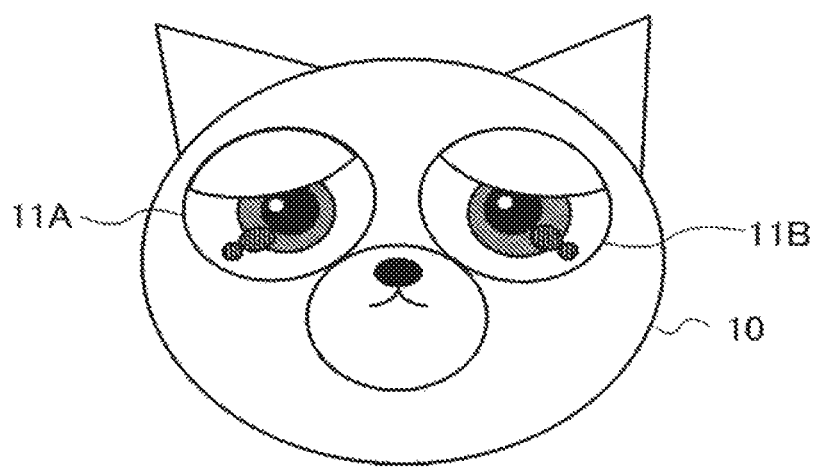
FIG. 14 is a diagram showing a display example when expressing a state of weeping while watching a communication partner.

Next, a modification of the above-described embodiment will be described. In the above-described embodiment, the gaze motion generation unit 120 generates a gaze motion corresponding to environment information acquired by the environment information acquisition unit 110. However, the gaze motion generation unit 120 may generate a gaze motion based on a dialogue content, not limited to environment information. That is, the gaze motion generation unit 120 may further generate a gaze motion corresponding to a dialogue content determined by the dialogue determination unit 100. Consequently, for example, it is possible to distinguish between expression of sorrow sympathizing with a communication partner and expression of spontaneous sorrow of the communication device 1. This will be explained showing specific examples. For example, when it is determined by the dialogue determination unit 100 that the communication device 1 is scolded by a communication partner, the gaze motion generation unit 120 generates a gaze motion to direct a line of sight toward a direction of other than the communication partner. Then, the gaze motion selection unit 142 selects as an expression object the gaze motion to direct the line of sight toward the direction of other than the communication partner, while the feeling determination unit 141 selects sorrow as an expression object. Consequently, as shown in FIG. 12 or FIG. 13, it is possible to express a state of weeping without looking into the eyes of the communication partner. FIG. 12 shows a display example of weeping with the line of sight directed laterally, and FIG. 13 shows a display example of weeping while looking down. In this way, it is possible to express spontaneous sorrow. On the other hand, for example, when it is determined by the dialogue determination unit 100 that a communication partner is injured and feels sad, the gaze motion generation unit 120 generates a gaze motion to direct a line of sight toward a direction of the communication partner. Then, the gaze motion selection unit 142 selects as an expression object the gaze motion to direct the line of sight toward the direction of the communication partner, while the feeling determination unit 141 selects sorrow as an expression object. Consequently, as shown in FIG. 14, it is possible to express a state of weeping while watching the communication partner. In this way, it is possible to express sorrow based on sympathy.

According to this modification, it is possible to display a line of sight corresponding to a dialogue content alone with a feeling. Therefore, expression of the feeling can be assisted by the line of sight corresponding to the dialogue content, so that feeling expression can be made rich. That is, since facial expression can be controlled more delicately, it is possible to reproduce feeling expression like a real animal.

The present disclosure is not limited to the above-described embodiment and modification and can be changed as appropriate within a range not departing from the gist of the present disclosure. For example, in the above-described embodiment, gaze motions are generated based on environment information about the movement of an object and the generation of a sound, but the present disclosure is not limited thereto. As environment information, other information such as the smell and the temperature may be used.

What is claimed is:

1. A communication device comprising:
    a face portion;
    a display provided in the face portion;
    an environment measuring device configured to acquire environment information being information about an environment around the communication device, the environment information including a first direction in which a communication partner is present and a second direction in which a moving object other than the communication partner is present; and
    a control device configured to
        generate a gaze motion of the communication device to be expressed in the face portion, the gaze motion corresponding to the environment information and including a first gaze motion being a gaze motion to be directed toward the first direction and a second gaze motion being a gaze motion to be directed toward the second direction;
        select one of the first gaze motion and the second gaze motion;
        generate, according to a predetermined generation rule, a feeling of the communication device to be expressed in the face portion; and
        display on the display an image of an eye expressing the selected gaze motion and the generated feeling.

2. The communication device according to claim 1, wherein in a case where an image of a closed eye is displayed on the display when the environment measuring device acquires the environment information about the moving object, the control device is configured to
    not select the second gaze motion directed toward the second direction in which the moving object is present, and
    display on the display the image of the eye expressing the generated feeling.

3. The communication device according to claim 1, wherein
    the environment information includes a third direction being a direction of a sound generated in the environment around the communication device, and
    the control device is configured to
        generate a third gaze motion being a gaze motion to be directed toward the third direction;
        select one of the first gaze motion, the second gaze motion, and the third gaze motion; and
        display on the display the image of the eye expressing the selected gaze motion and the generated feeling.

4. The communication device according to claim 1, wherein the control device is configured to select the first gaze motion when the generated feeling corresponds to a predetermined feeling.

5. The communication device according to claim 1, wherein the control device is configured to
    determine a dialogue content with the communication partner; and
    generate a third gaze motion corresponding to a determined dialogue content.

6. The communication device according to claim 1, wherein a display screen of the display has a size and a shape corresponding to a size and a shape of the eye that is expressed in the face portion.

7. The communication device according to claim 6, wherein the display screen is formed in only portions of the face portion corresponding to eyes that are expressed in the face portion.

8. The communication device according to claim 1, wherein portions of the face portion other than the display are formed by realistic members resembling components of the face.

9. The communication device according to claim 1, wherein the environment measuring device is disposed in a nose member of the face portion.

10. The communication device according to claim 1, wherein the control device is configured to
    generate a third gaze motion being a gaze motion to search for the communication partner when the communication partner is not found; and
    display on the display an image of the eye expressing the third gaze motion and the generated feeling.

11. The communication device according to claim 1, wherein the generated feeling is a spontaneous feeling corresponding to an internal state of the communication device.

12. The communication device according to claim 1, wherein the control device is configured to
    generate a plurality of feelings simultaneously,
    apply a weight to each of the plurality of feelings,
    determine one feeling by integrating the plurality of feelings based upon the weights.

13. The communication device according to claim 1, wherein the control device is configured to select the one of the first gaze motion and the second gaze motion based upon the generated feeling.

14. The communication device according to claim 1, wherein the control device is configured to select the one of the first gaze motion and the second gaze motion based upon the environment information.

15. The communication device according to claim 3, wherein the control device is configured to select the one of the first gaze motion, the second gaze motion, and the third gaze motion based upon a dialogue duration period with the communication partner.

* * * * *